(12) United States Patent
Pugliano et al.

(10) Patent No.: US 11,246,755 B2
(45) Date of Patent: Feb. 15, 2022

(54) SOUND ATTENUATION EARPLUG SYSTEM AND METHOD OF MANUFACTURE

(71) Applicant: Microsonic, Inc., Ambridge, PA (US)

(72) Inventors: Monika Pugliano, Ambridge, PA (US); Ozden Uslu, Ambridge, PA (US)

(73) Assignee: Microsonic, Inc., Ambridge, PA (US)

(\*) Notice: Subject to any disclaimer, the term of this patent is extended or adjusted under 35 U.S.C. 154(b) by 886 days.

(21) Appl. No.: 15/817,141

(22) Filed: Nov. 17, 2017

(65) Prior Publication Data

US 2019/0151153 A1 May 23, 2019

(51) Int. Cl.
| | | |
|---|---|---|
| *A61F 11/08* | (2006.01) | |
| *B29C 64/393* | (2017.01) | |
| *B29C 64/106* | (2017.01) | |
| *B33Y 10/00* | (2015.01) | |
| *B33Y 80/00* | (2015.01) | |
| *B33Y 50/02* | (2015.01) | |
| *B29L 31/00* | (2006.01) | |

(52) U.S. Cl.
CPC ............ *A61F 11/08* (2013.01); *B29C 64/106* (2017.08); *B29C 64/393* (2017.08); *B33Y 10/00* (2014.12); *B33Y 50/02* (2014.12); *B33Y 80/00* (2014.12); *A61F 2240/002* (2013.01); *A61F 2240/004* (2013.01); *B29L 2031/753* (2013.01)

(58) Field of Classification Search
CPC .............................. H04R 25/02; H04R 1/1016; H04R 2225/025; A61B 17/00; A61F 11/00; A61F 11/008
USPC ........ 128/864, 866, 867, 865, 868; 181/130, 181/135
See application file for complete search history.

(56) References Cited

U.S. PATENT DOCUMENTS

| | | | |
|---|---|---|---|
| 2,619,960 A | 12/1952 | Reynolds | |
| 2,785,675 A | 3/1957 | Berkman | |
| 2,888,921 A | 6/1959 | Nielson et al. | |
| 3,303,902 A * | 2/1967 | Knott | H04M 1/2155 181/135 |
| 3,729,598 A | 4/1973 | Tegt et al. | |
| 4,055,233 A | 10/1977 | Huntress | |
| 4,094,315 A * | 6/1978 | Leight | A61F 11/08 128/864 |
| 4,311,206 A | 1/1982 | Johnson | |
| 4,372,904 A | 2/1983 | Gunn | |
| 4,442,917 A | 4/1984 | Johnson | |
| 4,629,833 A | 12/1986 | Kern et al. | |
| 4,811,402 A | 3/1989 | Ward | |

(Continued)

FOREIGN PATENT DOCUMENTS

EP 2055277 5/2009

*Primary Examiner* — Caitlin A Carreiro
(74) *Attorney, Agent, or Firm* — LaMorte & Associates, P.C.

(57) ABSTRACT

An earplug device that is placed in the ear canal to attenuate sound frequencies within a selected frequency range. The earplug has a plug body with a first end, an opposite second end, and an exterior surface that extends from the first end to the second end. An opening is formed in the plug body at the first end. The opening leads to an internal conduit within the plug body. The internal conduit terminates at a closed membrane wall proximate the second end of the plug body. The internal conduit and the membrane wall both act upon incoming acoustic signals to both lower volume and attenuate certain undesired frequency ranges.

14 Claims, 10 Drawing Sheets

(56) References Cited

U.S. PATENT DOCUMENTS

| Patent/Publication | Date | Inventor | Classification |
|---|---|---|---|
| 4,974,606 A | 12/1990 | Van Mierlo | |
| 5,832,094 A | 11/1998 | LeHer | |
| 6,006,857 A * | 12/1999 | Leight | A61F 11/08 128/864 |
| 6,129,175 A * | 10/2000 | Tutor | A61F 11/08 128/864 |
| 6,164,409 A * | 12/2000 | Berger | H04R 25/654 128/864 |
| 6,744,897 B1 | 6/2004 | Vonlanthen | |
| 7,079,662 B2 | 7/2006 | Niederdrank | |
| 7,542,581 B2 | 6/2009 | Baumann | |
| 7,740,104 B1 | 6/2010 | Parkins et al. | |
| 7,783,056 B2 | 8/2010 | Wilmink | |
| 7,983,433 B2 | 7/2011 | Nemirovski | |
| 8,019,107 B2 | 9/2011 | Ngia et al. | |
| 8,103,029 B2 | 1/2012 | Ngia et al. | |
| 8,155,338 B2 | 4/2012 | Wilmink | |
| 8,184,821 B2 | 5/2012 | Sung | |
| 8,295,503 B2 | 10/2012 | Sung et al. | |
| 8,327,973 B2 * | 12/2012 | Parish | B29C 44/5627 181/129 |
| 8,422,719 B2 | 4/2013 | Dedieu et al. | |
| 8,903,114 B2 | 12/2014 | Voix et al. | |
| 8,923,523 B2 | 12/2014 | Bouhraoua | |
| 8,983,103 B2 | 3/2015 | Vlach et al. | |
| 9,198,800 B2 | 12/2015 | Killion et al. | |
| 9,210,522 B2 | 12/2015 | Obradovic et al. | |
| 2003/0116165 A1 * | 6/2003 | Huang | A61F 11/08 128/864 |
| 2003/0159878 A1 | 8/2003 | Hakansson | |
| 2003/0174846 A1 | 9/2003 | Niederdrank | |
| 2005/0196004 A1 | 9/2005 | Baumann et al. | |
| 2006/0042867 A1 | 3/2006 | Haussmann et al. | |
| 2007/0086599 A1 | 4/2007 | Wilmink | |
| 2007/0121974 A1 | 5/2007 | Nemirovski | |
| 2007/0125590 A1 | 6/2007 | Oberdanner | |
| 2007/0228714 A1 | 10/2007 | Bowers | |
| 2007/0230734 A1 | 10/2007 | Beard | |
| 2009/0190771 A1 | 7/2009 | Sung | |
| 2009/0208047 A1 | 8/2009 | Ngia | |
| 2009/0209304 A1 | 8/2009 | Ngia | |
| 2009/0220103 A1 | 9/2009 | Wilmink | |
| 2010/0215198 A1 | 8/2010 | Mgia | |
| 2011/0081035 A1 | 4/2011 | Dedieu | |
| 2011/0235816 A1 | 9/2011 | Bouhraoua | |
| 2011/0255723 A1 | 10/2011 | Obradovic | |
| 2013/0056295 A1 * | 3/2013 | Campbell | H04R 25/652 181/135 |
| 2014/0309597 A1 * | 10/2014 | Lowney | A61F 11/00 604/285 |

* cited by examiner

SOUND ATTENUATION EARPLUG SYSTEM AND METHOD OF MANUFACTURE

BACKGROUND OF THE INVENTION

1. Field of the Invention

In general, the present invention relates to sound attenuation devices that are inserted into the auditory canal of the ear. More particularly, the present invention is related to sound attenuation devices that have a predictable control over the level of sound attenuation across specific hearing frequencies.

2. Prior Art Description

In an attempt to reduce the level of perceived noise, people often obstruct the auditory canals of their ears. Individuals have placed materials, such as cotton or paper fibers, into their ears for centuries. Such material easily conforms to the shape of the auditory canal. However, such materials rarely form a complete seal. Accordingly, loud sounds can still be perceived at levels that could damage the ear. In order to reduce noise levels, more and more material is packed into the auditory canal in an attempt to create a seal. Eventually, the material can be pushed against the ear drum and cause pain or hearing damage.

In modern times, more sophisticated earplugs are available. Such earplugs are typically amorphous or fixed. Amorphous earplugs include soft materials, such as silicone or soft foam. These amorphous materials are sold in small volumes that are just large enough to obstruct the ear canal. Such amorphous materials are inserted into the auditory canal and can seal the auditory canal. However, the shape of the auditory canal changes a person moves his/her mandible. Accordingly, as an individual moves, talks, eats and otherwise moves their mandible, the shape of the auditory canal is changed. As the shape of the auditory canal changes, the amorphous material becomes deformed and gaps appear around the material. The gaps create openings which loud sounds can propagate.

This problem has been partially solved by using custom molded earplugs that are molded to the anatomy of a user's ear. However, the set shape of the material is often too resilient to adapt to continuous movement of the auditory canal. The mandibular movement of the user will cause the earplug to move in and out of the ear. The result is that the earplug loosens and gaps form through which loud sounds can propagate.

The one advantage of fix molded earplugs is that they can be engineered to attenuate certain frequency ranges. Such precision earplugs are typically manufactured with an internal sound attenuating filter. Such prior art is exemplified by European Patent No. EP2055277 to Oberdanner and U.S. Pat. No. 5,832,094 to Leher. The problem with such earplugs is twofold. First, the need for an attenuation filter makes the earplug difficult to insert into narrow ear canals. Second, such earplugs have an opening in their structure that faces the eardrum. This opening can, and commonly does, become blocked with cerumen. Once this happens, the engineered characteristics of the earplug are compromised and the intended attenuation level is distorted. As a result, the hearing protection device does not perform as intended and the user is likely to avoid using the device. Acoustic filters may also become loose over time and fall into the ear canal which can cause a serious health hazard.

A need therefore exists for an improved earplug system that can form a better seal within the auditory canal, that delivers noise attenuation as intended, and that cannot be fouled by cerumen or other debris. This need is met by the present invention as described and claimed below.

SUMMARY OF THE INVENTION

The present invention is an earplug device that is placed in the ear canal to attenuate sound frequencies within a selected frequency range. The earplug has a plug body. The plug body has a first end, an opposite second end, and an exterior surface that extends from the first end to tie second end. The exterior surface can be shaped to fit an average ear or can be custom molded to the anatomy of a specific person.

An opening is formed in the plug body at the first end. The opening leads to an internal conduit within the plug body. The internal conduit terminates at a closed membrane wall proximate the second end of the plug body. The internal conduit and the membrane wall both act upon incoming acoustic signals to both lower volume and attenuate certain undesired frequency ranges.

BRIEF DESCRIPTION OF THE DRAWINGS

For a better understanding of the present invention, reference is made to the following description of exemplary embodiments thereof, considered in conjunction with the accompanying drawings, in which.

DETAILED DESCRIPTION OF THE DRAWINGS

Although the present invention earplug system is typically sold in pairs for protecting both the left ear and the right ear, only one earplug is herein illustrated and described. It will be understood that the second earplug for the full set would have a mirrored geometry and would be manufactured and utilized in the same manner. The illustrated embodiment is selected for simplicity of description and represents one of the best modes contemplated for the invention. The illustrated embodiment, however, is merely exemplary and should not be considered a limitation when interpreting the scope of the appended claims.

Figure 1:
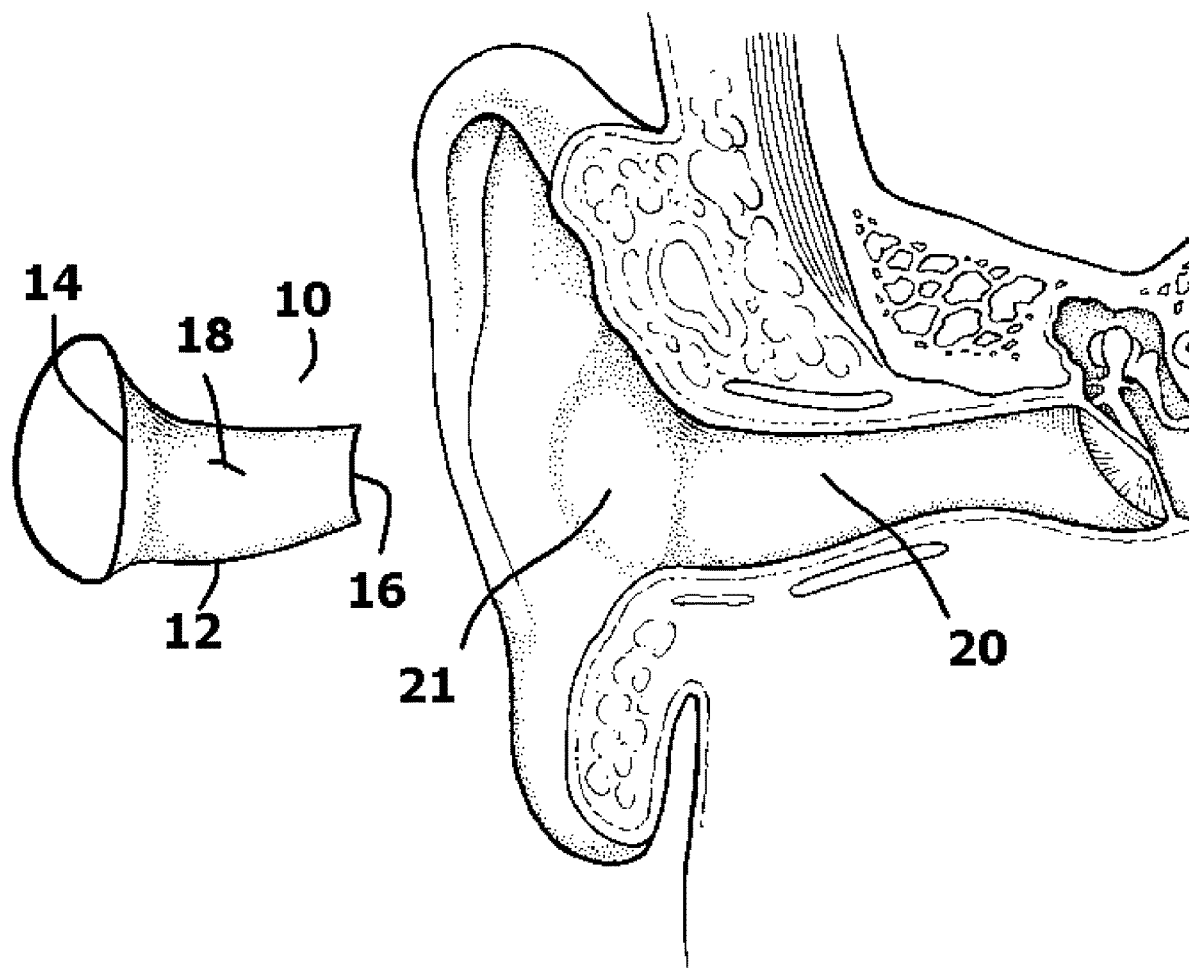
FIG. 1 is a side view of an exemplary embodiment of an earplug shown in conjunction with the auditory canal of an ear.
Figure 2:
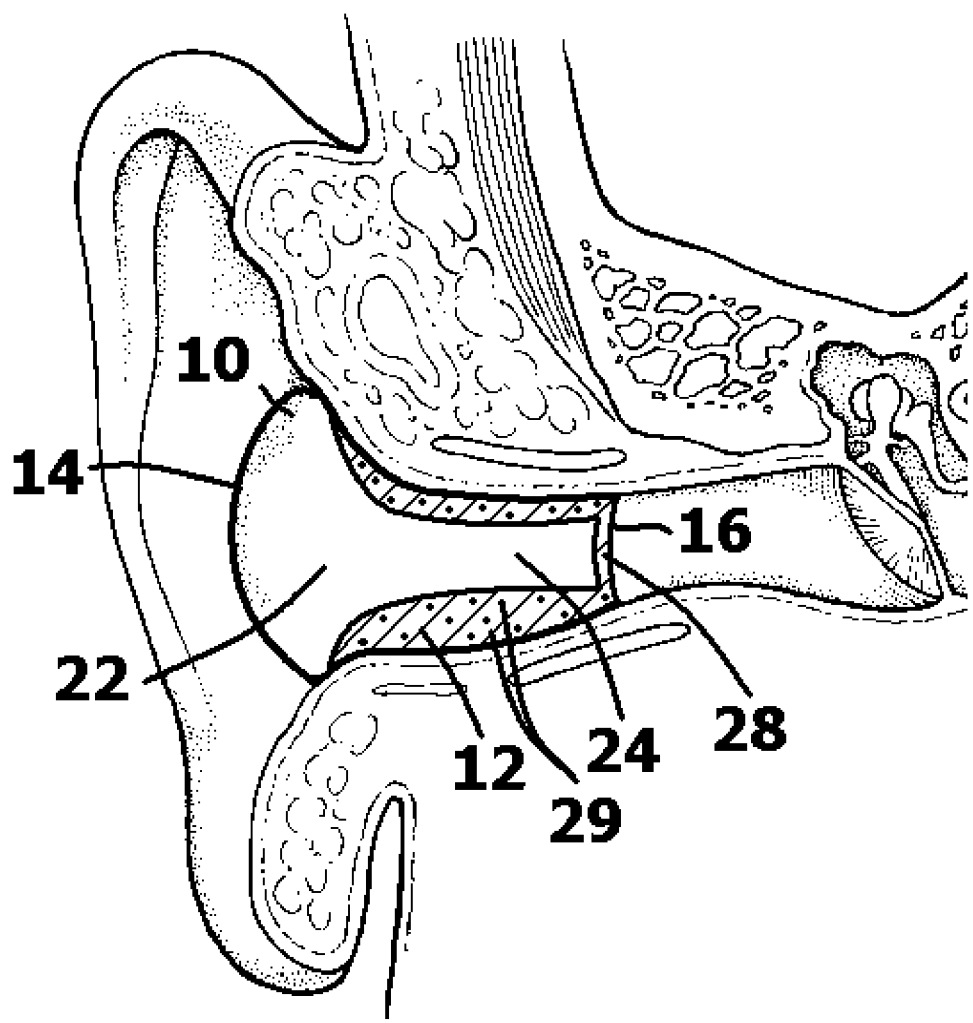
FIG. 2 is a cross-sectional view of the embodiment of the earplug of FIG. 1, shown engaged within the auditory canal.
Figure 3:
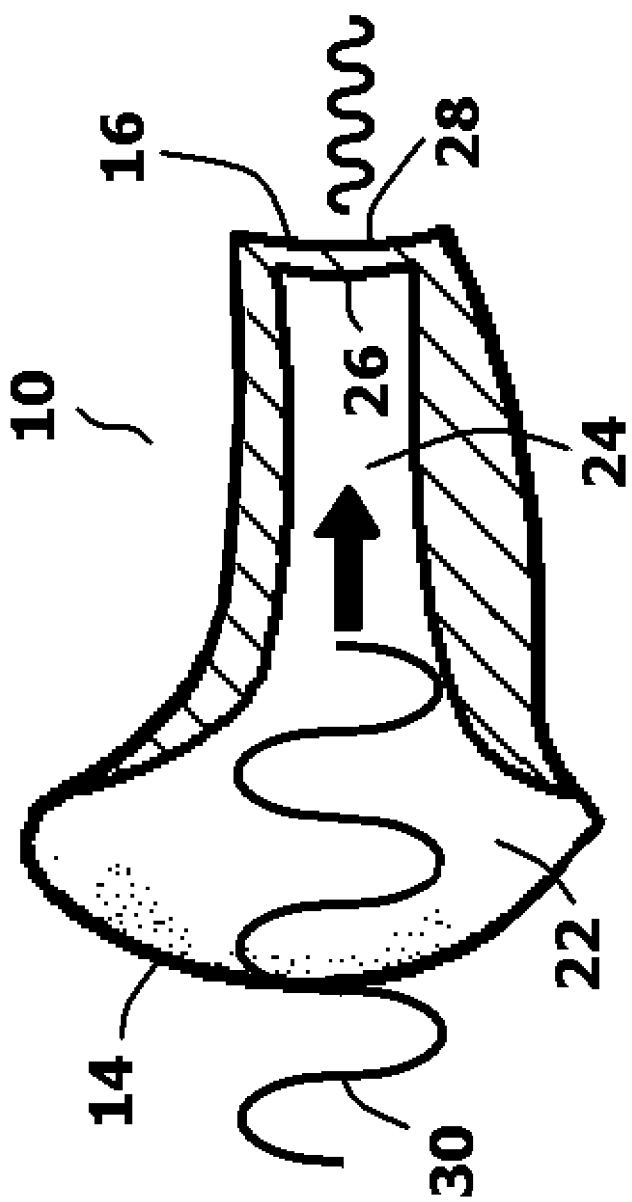
FIG. 3 shows an enlarged cross-sectional view of the exemplary earplug in conjunction with an incoming audio signal.

Referring to FIG. 1 in conjunction with FIG. 2 and FIG. 3, an earplug 10 is shown. The earplug 10 has a molded plug body 12 that is generally horn shaped. That is, the plug body 12 has a first end 14 with a large diameter and a second end 16 with a small diameter, like the horn of a trumpet. However, each individual has a unique ear shape. Custom molded plug body 12 made for some individuals present more uniform shape. The plug body 12 has an exterior surface 18. The exterior surface 18 is anatomically shaped so that it conforms the contours of the outer ear canal 20 and the incisura 21 that leads into the outer ear canal 20.

The plug body 12 can be injection molded from a soft elastomeric material, custom molded using a soft curable polymer, or fabricated using 3D printing techniques. The plug body 12 of the earplug 10 contacts the skin of the ear across the entire exterior surface 18 of the plug body 12. As such, there is substantial material-to-ear contact across the entire exterior surface 18 of the earplug 10 from the first end 14 to the second end 16. The result is that although mandible movement of the user may create temporary gaps in the material-to-ear contact, the gaps are localized. The elastic nature of the plug body and the hollow design created by tie internal channel 24 ensures that the gaps never extend completely from the first end 14 to the second end 16. Accordingly, the integrity of the earplug 10 is not compromised and no sound energy can pass into the ear unattenuated.

There is no opening that extends completely through the plug body 12 of the earplug 10. Rather, there is a bell opening 22 at the first end 14 of the plug body 12. The bell opening 22 tapers down into an internal channel 24 that travels through the plug body 12 toward the second end 16. As will be later explained in more detail, the dimensions and length of the internal channel 24 are designed to produce an acoustic waveguide. The diameter of the internal channel 24 limits the amplitude of any acoustic signal entering the waveguide. The average diameter can be varied between 0.5 mm and 10.00 mm depending upon the size of the plug body 12 and the level of amplitude diminution desired. The distal end 26 of the internal channel 24, opposite the bell opening 22, is closed by a membrane wall 28. Accordingly, some of the acoustic energy that enters the internal channel 24 strikes the membrane wall 28 and is reflected back toward the bell opening 22. This reflected sound wave energy tends to interact with the incoming acoustical sound energy in an interference pattern that reduces the amplitude of the incoming sound energy. The result is a significant reduction in acoustical amplitude, which results in a corresponding reduction in sound volume.

The membrane wall 28 is engineered to create a specific level of amplitude and frequency filtering above and beyond that created by the dimensions of the internal channel 24. The thicker the membrane wall 28, the more sound energy is absorbed. Likewise, the thicker the membrane wall 28, the more acoustical energy is reflected back into the internal channel 24. The preferred thickness of the membrane wall 28 is between 0.2 mm and 11.50 mm depending upon the application. The greater the level of dangerous noise, the thicker the membrane wall 28 should be.

The plug body 12 is preferably formed from elastic polymers such as silicone, polyurethane, polychloroprene, and polyvinyl chloride (PVC). The elastic polymers have innate acoustical properties that enable the materials to absorb and reflect various sound frequencies. The ability of the elastic polymer to absorb and/or reflect specific sound frequencies may be supplemented by adding certain additives to the elastic polymer in controlled amounts. Additives, such as microspheres 29 can be mixed into the elastic polymer. The microspheres 29 can be solid or hollow and be made of glass or a plastic that has a higher melting point than that of the elastic polymer. Typically, the mean spherical particle size for the microspheres varies between 10 microns to 300 microns. Microspheres 29 of different materials and different sizes alter the absorptive and reflective properties of the curable polymer in different ways for different frequencies.

Figure 4:
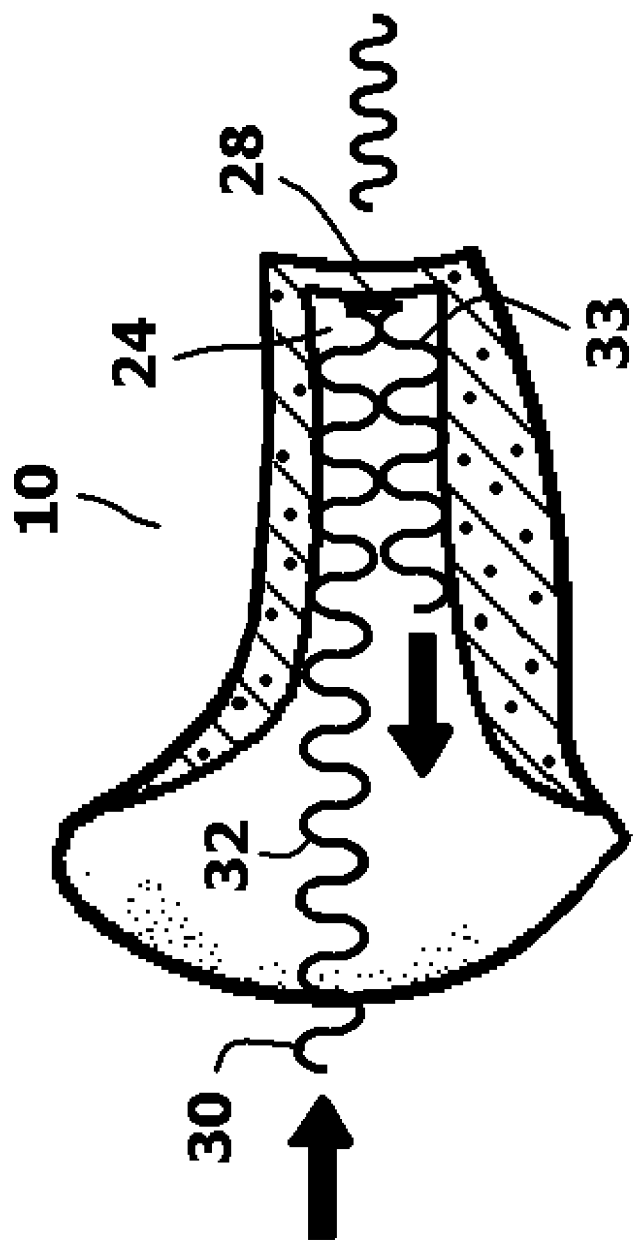
FIG. 4 shows an enlarged cross-sectional view of the exemplary earplug in conjunction with an incoming audio signal and a reflected signal.

Referring to FIG. 4, it will be understood that addition to the composition of the molded body 12, both the structure of the internal channel 24 and the structure of the membrane wall 28 that terminates the internal channel 24, can be used to attenuate incoming audio signals 30. The degree of attenuation, however, can be controlled. Since the internal channel 24 and the membrane wall 28 together form an acoustic waveguide structure, it will be understood that these elements can be resonance tuned to attenuate specific frequency ranges. This is accomplished by incoming audio signals 30 within specific frequency ranges will be efficiently absorbed and/or reflected by altering the dimensions of the internal channel 24 and the thickness of the membrane wall 28. This is achieved, in part, by having the incoming audio signals 30 impinge upon the membrane wall 28 at or near the largest amplitude of its waveform 32. This causes a reflected waveform 33 in an inverted phase to the incoming acoustic signals 30. The waveforms 32, 33 cancel each other and amplitude reduction is accomplished. Accordingly, the length of the internal channel 24 should not be at or near a positive integer multiple of the undesired frequencies contained within the incoming audio signal 30.

Figure 5:
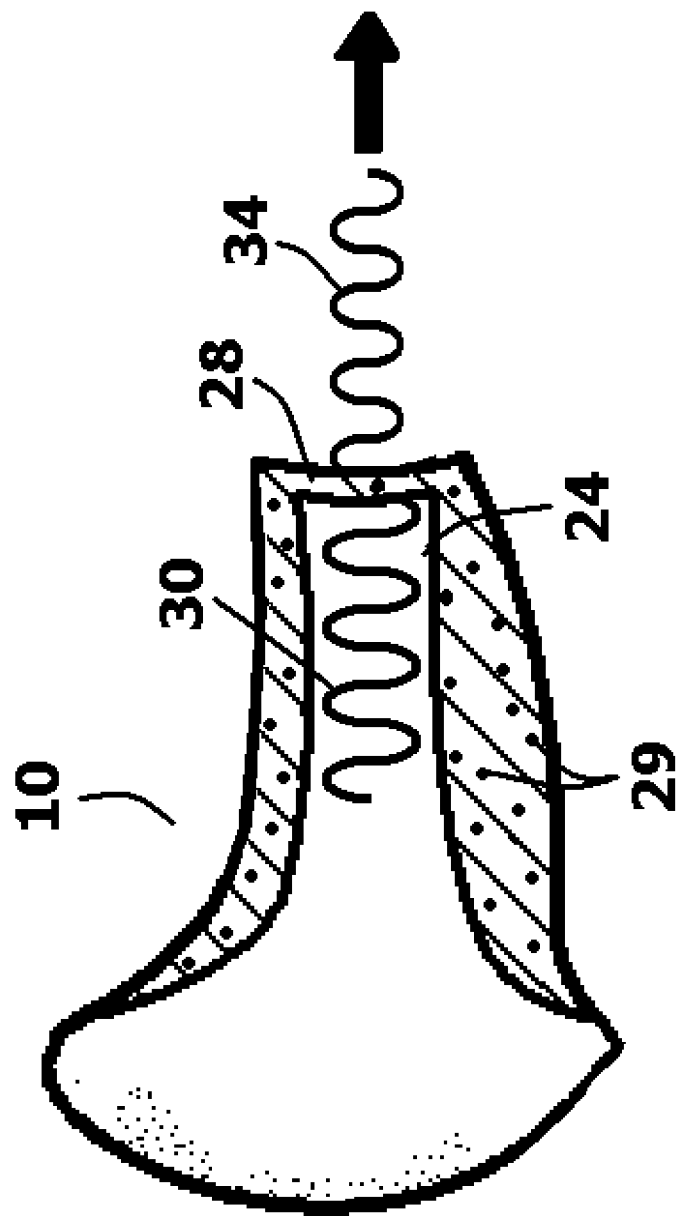
FIG. 5 shows an enlarged cross-sectional view of the exemplary earplug in conjunction with an incoming audio signal unattenuated by reflection.
Figure 6:
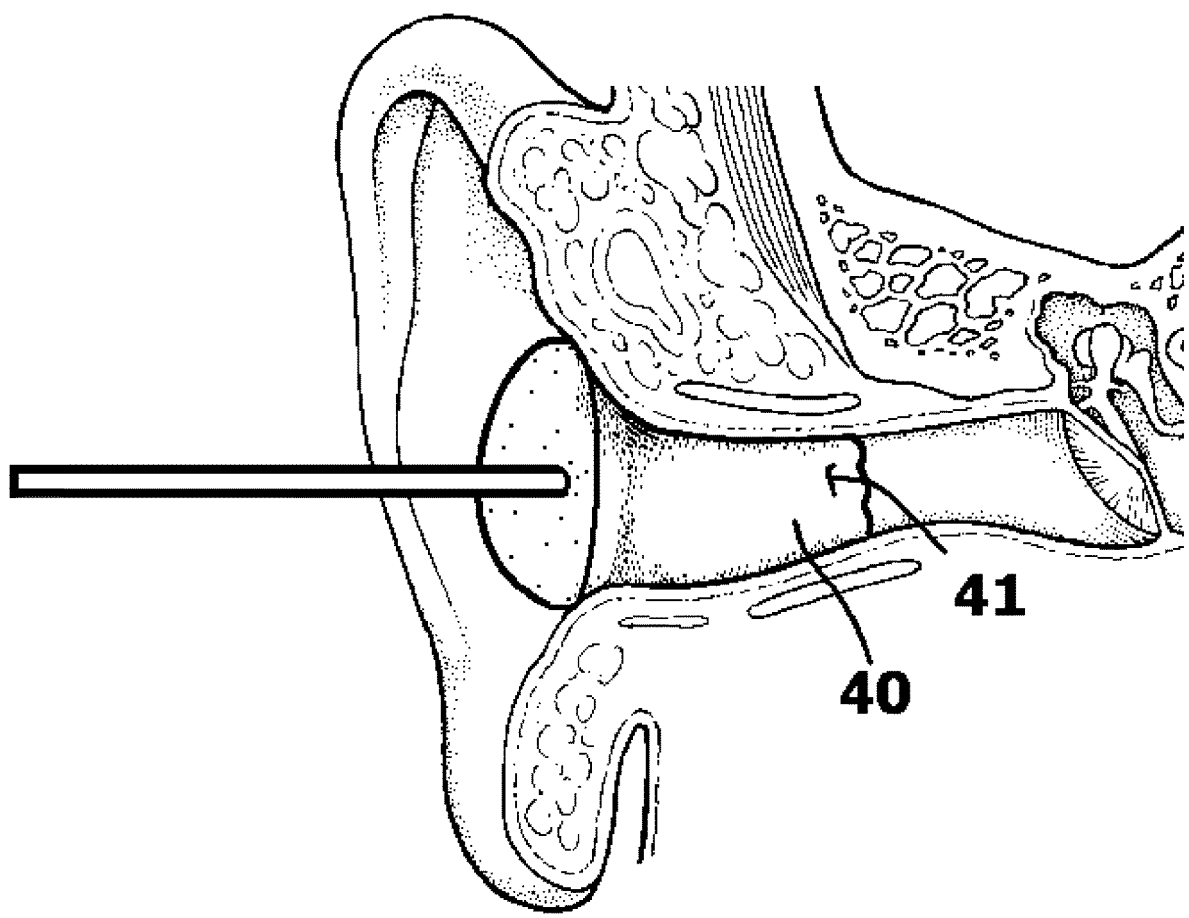
FIG. 6 shows a first step in the manufacturing process of a custom earplug.
Figure 7:
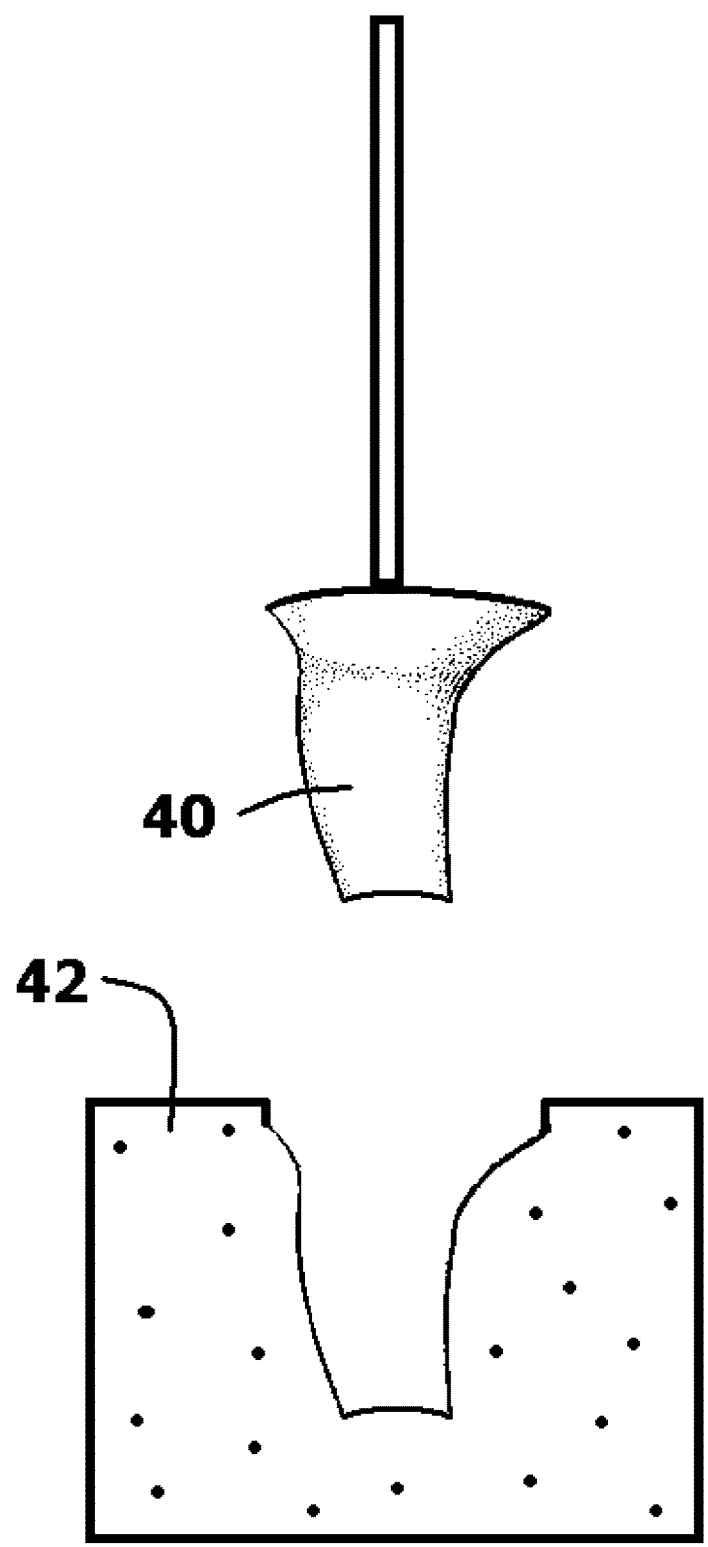
FIG. 7 shows a second step in the manufacturing process of a custom earplug.
Figure 8:
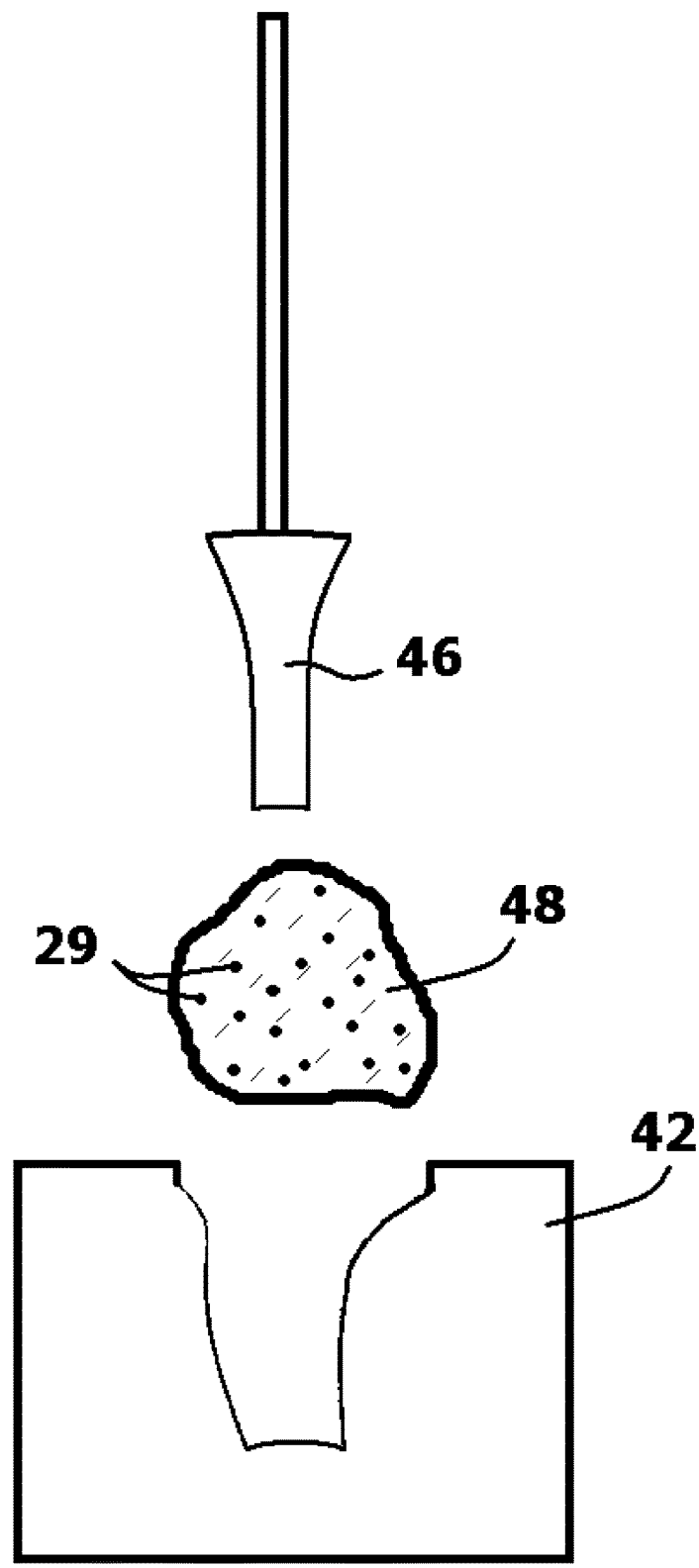
FIG. 8 shows a third step in the manufacturing process of a custom earplug.
Figure 9:
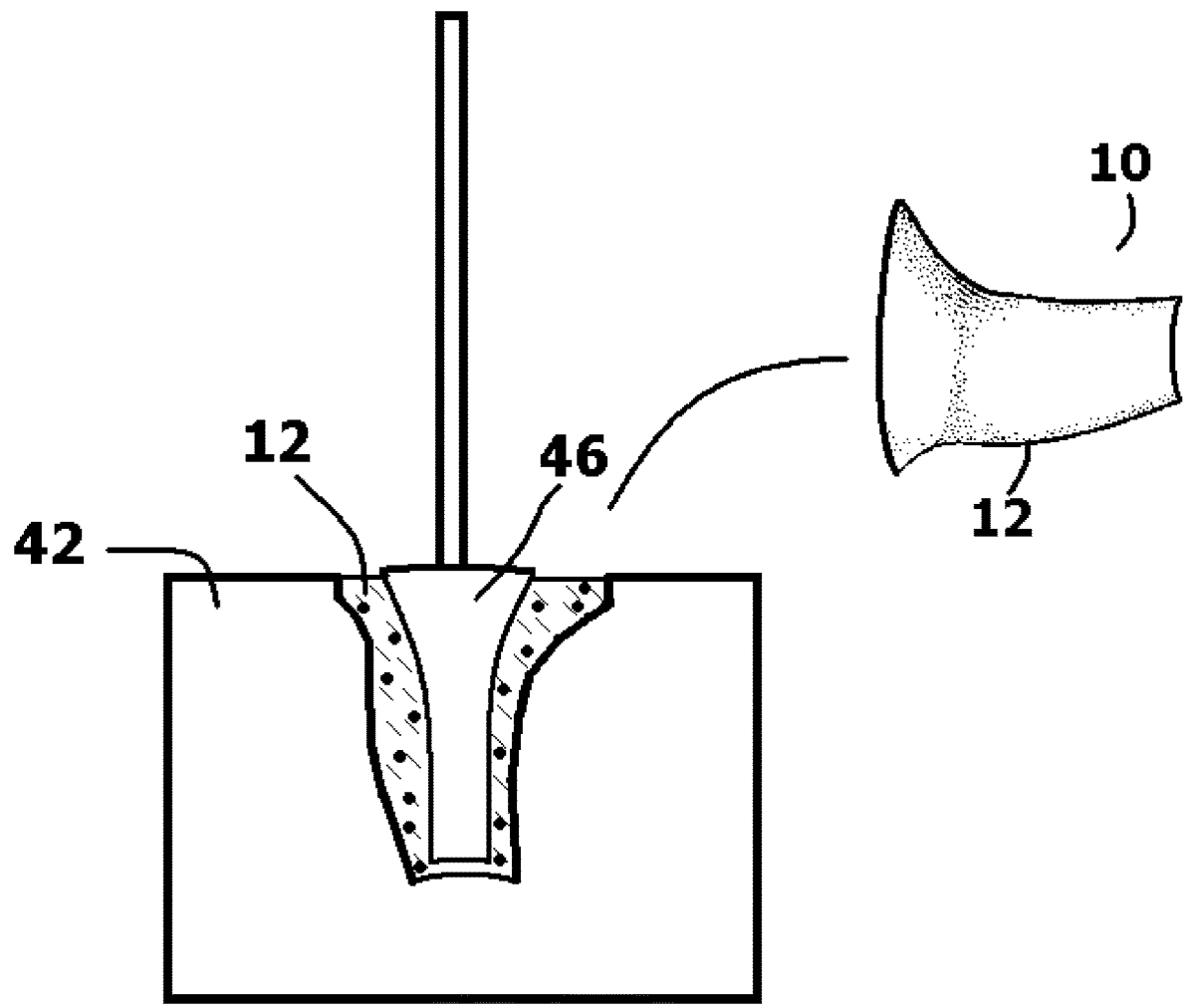
FIG. 9 shows a final step in the manufacturing process of a custom earplug.

Referring to FIG. 5, it will also be understood that the dimensions of the internal channel 24 and the thickness of the membrane wall 28 can also be designed to allow certain frequencies within the incoming audio signals 30 to pass. Compounding appropriate size and type of microspheres 29 into material can improve the frequency filtering aspect of the membrane wall 28. The length of the inter al channel 24 is controlled so that desirable frequencies within the incoming audio signals 30 travel through the internal channel 24 and impinge upon the membrane wall 28 near a null in the frequency waveform 34. This prevents the creation of an out-of-phase reflection and the incoming audio signals 30 can pass through the earplug 10 losing only the energy that is absorbed by the membrane wall 28. This can be accomplished by making the length of the internal chamber 24 a positive integer multiple of a desirable frequency that is to pass. In this manner, it will be understood that earplugs 10 can be custom designed to attenuate acoustic signals in certain frequency ranges but enable a person to hear other acoustic signals in desirable frequency ranges.

From the above, it will be understood that to have the internal channel 24 and the membrane wall 28 act as a tuned acoustic waveguide, the internal channel 24 and the membrane wall 28 must be manufactured to precise dimensions.

Referring to FIG. 6, FIG. 7, FIG. 8 and FIG. 9, it can be seen that one method of creating the earplug 10 is to custom mold the earplug 10 in one technique, an impression 40 of the auditory canal is taken using a traditional impression material 41. The impression 40 is measured to determine the size limits or any other physical restraints that have to be applied to the formation of the internal cannel and the membrane wall within the earplug 10. See FIG. 6.

Once the impression 40 is cured, the impression 40 is utilized to create a formation mold 42. See FIG. 7. A mold insert 46 is then created using the physical limitations presented by the dimensions of the impression 40. The mold insert 46 embodies the desired dimensions of the bell opening, internal channel and membrane wall. See FIG. 8.

A volume of a soft curable polymer 48 is introduced into the formation mold 42. The curable polymer 48 has previously been mixed with the desired type and concentration of microspheres 29. The mold insert 46 is set into the curable polymer 48 so that the curable polymer 48 is molded between the mold insert 46 and the formation mold 42. See FIG. 9. Once the curable polymer 48 cures, the resulting plug body 12 is trimmed of flash. Typically, a handle or cord (not shown) is added to the earplugs 10 to make them easy to handle, insert and remove. At this point, the earplug 10 is complete and ready for use. If desired, the earplug 10 can be finished to become less noticeable in the ear or more aesthetically pleasant.

Figure 10:
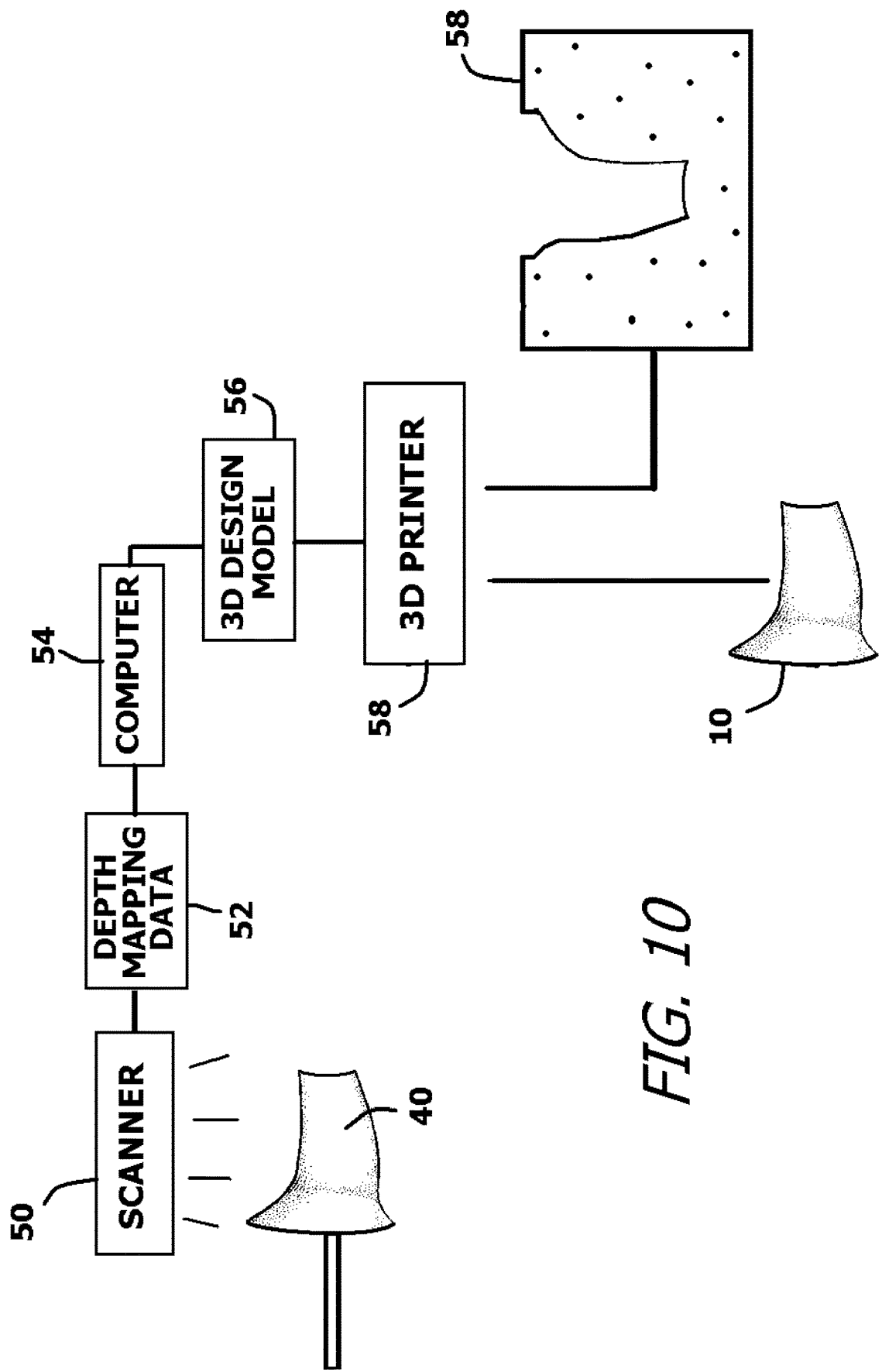
FIG. 10 shows an alternate manufacturing process of a custom earplug that utilizes a 3D printer for fabrication.

Referring to FIG. 10, an alternate method of manufacturing a custom-fitted earplug 10 is explained. In a first step, an impression 40 of the auditory canal is taken in a traditional manner. The impression 40 is scanned by a scanner 50 to collect depth mapping data 52. The depth mapping data 52 corresponds to the complex shape of the impression 40. Next, the depth mapping data 52 is utilized to generate a 3D design model 54 using commercial 3D modeling software. Once the 3D design model 54 is created, the internal canal can be designed into that model, taking into account the virtual boundaries embodied by the 3D design model 54. The internal conduit is designed to produce specific acoustic attenuation. This results in a final virtual design.

The final virtual design is then downloaded into a 3D printer 56. The 3D printer 56 is then used to either create the earplug 10 directly or to print a mold 58 for the earplug 10. If the 3D printer is used to directly print the earplug 10, then the earplug 10 must be fabricated from one of the materials are compatible with 3D printing machines. However, if the 3D printer 56 is used to create a mold. 58 for the earpiece 10, then the mold 58 is later filled with any curable soft polymer, regardless to whether it is 3D printer compatible or not. In this manner, polymers mixed with microspheres can be used.

In an alternative method of manufacture, the earplug 10 need not be custom manufactured. Rather, the earplug 10 can be mass produced using injection molding. The earplug 10 can be molded in a variety of sizes, such as small, medium and large. Using such a manufacturing technique, the earplug 10 can be mass produced for average people who have average ear anatomy. Such techniques will cause the earplug 10 to fit better on some people than on others. However, the earplugs 10 can be mass produced at low cost. Accordingly, the earplugs 10 can be marketed at low cost for disposable purposes, such as for use at music concerts or sporting events.

It will be understood that the embodiments of the present invention that are illustrated and described are merely exemplary and that a person skilled in the art can make many variations to those embodiments. All such embodiments are intended to be included within the scope of the present invention as defined by the claims.

What is claimed is:

1. An earplug device configured for placement in an ear canal to attenuate sound frequencies within a selected frequency range, said device comprising:
    a plug body having an open first end, a closed second end, opposite to said first end, and an exterior surface that extends from said first end to said second end, said first end having a first diameter and said second end having a second diameter wherein said first diameter is greater than said second diameter, wherein said exterior surface is anatomically shaped to conform to the ear canal and is configured to provide substantial material-to-ear contact across the entire exterior surface of said plug body from said first end to said second end to prevent gaps from extending completely from said first end to said second end, thereby preventing sound energy from passing through unattenuated;
    an internal channel having a constant diameter from end to end, wherein said internal channel is provided within said plug body and terminates at a membrane wall proximate said second end of said plug body, wherein said internal channel and said membrane wall form an acoustic waveguide structure within said plug body that is resonance tuned to attenuate sound frequencies within said selected frequency range; and
    a bell opening having a largest diameter at said first end of said plug body that gradually and continuously narrows in a direction extending towards said second end of said plug body such that said bell opening tapers down into said internal channel within said plug body to provide a continuous hollow passageway from said bell opening at said first end, through said internal channel, to said membrane wall proximate said second end.

2. The device according to claim 1, wherein said plug body is molded from curable polymers, wherein said curable polymers are selected from a group consisting of silicone, polyurethane, polychloroprene, and polyvinyl chloride.

3. The device according to claim 2, wherein said curable polymers have acoustic characteristics in said earplug device and said curable polymers are mixed with a volume of microspheres, wherein said microspheres alter acoustic characteristics associated with said curable polymers.

4. The device according to claim 1, wherein said membrane wall has a thickness between 0.2 mm and 11.50 mm.

5. The device according to claim 1, wherein said internal channel has a diameter between 0.5 mm and 10.00 mm.

6. An earplug device configured for placement in an ear canal for attenuating sound frequencies within a selected frequency range, said device comprising:
    a plug body having an open first end, a closed second end, opposite to said first end, and an exterior surface, said first end having a first diameter and said second end having a second diameter wherein said first diameter is greater than said second diameter, wherein said exterior surface is configured to provide substantial material-to-ear contact across the entire exterior surface of said plug body from said first end to said second end to prevent gaps from extending completely from said first end to said second end, thereby preventing sound energy from passing through unattenuated;
    an internal conduit having a constant diameter from end to end, wherein said internal conduit is disposed within said plug body and terminates at a solid membrane wall proximate said second end of said plug body, wherein said internal conduit and said solid membrane wall form an acoustic waveguide structure within said plug body that is resonance tuned to attenuate sound frequencies within said selected frequency range; and
    a bell opening formed in said first end of said plug body and having a largest diameter at said first end of said plug body that gradually and continuously narrows in a direction extending towards said second end of said plug body such that said bell opening tapers down from said first end of said plug body into said internal conduit within said plug body to provide a continuous hollow passageway from said bell opening at said first end, through said internal conduit, to said solid membrane wall proximate said second end.

7. The device according to claim 6, wherein said plug body is molded from curable polymers, wherein said curable polymers are selected from a group consisting of silicone, polyurethane, polychloroprene, and polyvinyl chloride.

8. The device according to claim 7, wherein said curable polymers have acoustic characteristics in said earplug device and said curable polymers are mixed with a volume of microspheres, wherein said microspheres alter acoustic characteristics associated with said curable polymers.

9. The device according to claim 6, wherein at least part of said exterior surface has a shape configured to conform to the ear canal.

10. The device according to claim 6, wherein said solid membrane wall has a thickness between 0.2 mm and 11.50 mm.

11. The device according to claim 6, wherein said internal conduit has a diameter of between 0.5 mm and 10.00 mm.

12. An earplug device that is configured for placement in an ear canal to attenuate sound frequencies within a selected frequency range, said device comprising:
  a plug body having an open first end, a closed second end, opposite to said first end, and an exterior surface that is configured to conform in shape to the ear canal, said first end having a first diameter and said second end having a second diameter wherein said first diameter is greater than said second diameter, wherein said exterior surface is configured to provide substantial material-to-ear contact across the entire exterior surface of said plug body from said first end to said second end to prevent gaps from extending completely from said first end to said second end, thereby preventing sound energy from passing through unattenuated;
  an internal conduit molded into said plug body and having a constant diameter from end to end, wherein said internal conduit is only accessible from said first end of said plug body and terminates at a solid membrane wall proximate said second end of said plug body, wherein said internal conduit and said solid membrane wall form an acoustic waveguide structure within said plug body that is resonance tuned to attenuate said sound frequencies within said selected frequency range; and
  a bell opening having a largest diameter at said first end of said plug body that gradually and continuously narrows in a direction extending towards said second end of said plug body such that said bell opening tapers down into said internal conduit within said plug body to provide a continuous hollow passageway from said bell opening at said first end, through said internal conduit, to said solid membrane wall proximate said second end.

13. The device according to claim 12, wherein said plug body is molded from curable polymers, wherein said curable polymers are selected from a group consisting of silicone, polyurethane, polychloroprene, and polyvinyl chloride.

14. The device according to claim 12, wherein said solid membrane wall has a thickness between 0.2 mm and 11.50 mm.

* * * * *